(12) United States Patent
Ruan

(10) Patent No.: US 11,896,791 B2
(45) Date of Patent: Feb. 13, 2024

(54) ANUS CLEANER

(71) Applicant: Haiyong Ruan, Zhejiang (CN)

(72) Inventor: Haiyong Ruan, Zhejiang (CN)

(73) Assignee: Ningbo Dianai Plastic Co., Ltd., Zhejiang (CN)

( * ) Notice: Subject to any disclaimer, the term of this patent is extended or adjusted under 35 U.S.C. 154(b) by 314 days.

(21) Appl. No.: 17/375,001

(22) Filed: Jul. 14, 2021

(65) Prior Publication Data
US 2022/0088290 A1   Mar. 24, 2022

(30) Foreign Application Priority Data

Sep. 23, 2020 (DE) .......................... 202020105434.1

(51) Int. Cl.
*A61M 3/02* (2006.01)
*A61M 39/24* (2006.01)

(52) U.S. Cl.
CPC .......... *A61M 3/0262* (2013.01); *A61M 3/022* (2014.02); *A61M 39/24* (2013.01); *A61M 3/0245* (2013.01); *A61M 2039/248* (2013.01); *A61M 2039/2433* (2013.01)

(58) Field of Classification Search
CPC .. A61M 2205/075; A61M 1/682; A61M 1/82; A61M 13/0262
See application file for complete search history.

(56) References Cited

U.S. PATENT DOCUMENTS

| 1,261,608 A | * | 4/1918 | Peterson | ............... A61M 1/84 |
| | | | | 604/212 |
| 2002/0007156 A1 | * | 1/2002 | Miles | ............... A61M 39/24 |
| | | | | 604/246 |
| 2021/0023280 A1 | * | 1/2021 | Stanley | ............... A61M 3/0262 |

FOREIGN PATENT DOCUMENTS

| WO | WO-2010089368 A2 | * | 8/2010 | ......... A61M 1/0001 |
| WO | WO-2015000488 A1 | * | 1/2015 | ......... A61M 3/0262 |

* cited by examiner

*Primary Examiner* — Courtney B Fredrickson

(57) ABSTRACT

The invention discloses an anus cleaner, comprising a bottle body, wherein the inside of the bottle body is a hollow structure; the bottom of the bottle body is provided with a bottle bottom, and the bottle bottom is curved; the center of the bottle bottom is provided with a through hole, and a steel ball check valve is installed in the through hole; the end of the bottle body away from the bottle bottom is provided with a bottleneck, and the bottleneck is provided with threads; the bottleneck is equipped with a cleaning head; the bottom of the cleaning head is provided with threads, and the threads are provided on a mounting table; the mounting table and the bottleneck are matched and connected with the same size; the top of the mounting table is provided with a cleaning neck.

4 Claims, 10 Drawing Sheets

ANUS CLEANER

BACKGROUND OF THE INVENTION

1. Field of the Invention

The invention relates to the field of medical equipment, in particular to an anus cleaner.

2. Description of the Related Art

Enema is a treatment method that uses a catheter to be inserted from the anus through the rectum to the colon to infuse liquid to achieve laxative and exhaust. It can stimulate intestinal peristalsis, soften and clear feces, and has the function of cooling, inducing delivery, diluting intestinal poisons, reducing absorption, and low temperature solution for cooling patients with high fever; in addition, it can also achieve the purpose of supplying medicine, nutrition, water and other treatments. However, traditional anus cleaners do not have enough check valves to avoid the backflow of dirty water inside the anus, which will affect the cleanliness of the anus during use, thereby affecting the treatment process of the patient. Therefore, a cleaner that can effectively prevent anus regurgitation needs to be studied urgently.

SUMMARY OF THE INVENTION

The technical problem to be solved by the invention is to provide an anus cleaner with double check valves in view of the above problems.

In order to solve the above technical problems, the technical solutions provided by the invention are: an anus cleaner, comprising a bottle body, wherein the inside of the bottle body is a hollow structure; the bottom of the bottle body is provided with a bottle bottom, and the bottle bottom is curved; the center of the bottle bottom is provided with a through hole, and a steel ball check valve is installed in the through hole; the end of the bottle body away from the bottle bottom is provided with a bottleneck, and the bottleneck is provided with threads; the bottleneck is equipped with a cleaning head; the bottom of the cleaning head is provided with threads, and the threads are provided on a mounting table; the mounting table and the bottleneck are matched and connected with the same size; the top of the mounting table is provided with a cleaning neck; the inside of the cleaning head is provided with a flow channel; the end of the cleaning neck is provided with a liquid outlet; the center of the bottom of the mounting table is provided with a spring check valve, and the spring check valve communicates with the flow channel.

The advantageous effects of the invention compared with the prior art are: the invention can effectively prevent the backflow of the liquid inside the anus, which may cause pollution to the unused liquid medicine, thereby causing waste; the invention is clean and hygienic in use, does not cause secondary infections to patients, greatly improves the hygiene coefficient for patients with wounds in the anus, and has a good market prospect.

As an improvement, the bottom of the steel ball check valve is provided with a limiting seat; and the center of the bottom of the limiting seat is provided with an inlet; the inside of the steel ball check valve is provided with a cavity; the top of the limiting seat is fixed with limiting round tables, and the number of the limiting round table is two; the top of the limiting round table is fixed with a ball locking notch; the cavity inside the steel ball check valve is placed with a plugging steel ball the cavity is oval shaped, and both ends thereof can be matched with the plugging steel ball.

As an improvement, the bottom of the spring check valve is provided with a movable cavity, and the bottom of the movable cavity is provided with a limiting port; a spring base is installed inside the movable cavity on the limiting port, and a spring is installed on the spring base; the top of the spring is installed with a plugger; the top of the spring check valve is provided with a limiting ring, and the center of the limiting ring is provide with a limiting hole; the limiting hole is matched with the plugger; the bottom of the spring check valve is installed with a sealing ring.

As an improvement, the outside of the bottle body is a frosted surface, which is non-slip and easy to hold; the outside of the cleaning head has a smooth surface for easy access.

As an improvement, the cleaning neck is a tapered structure, and the diameter of the end thereof close to the liquid outlet is smaller than the end close to the mounting table, which is used to reduce discomfort.

Figure 1:
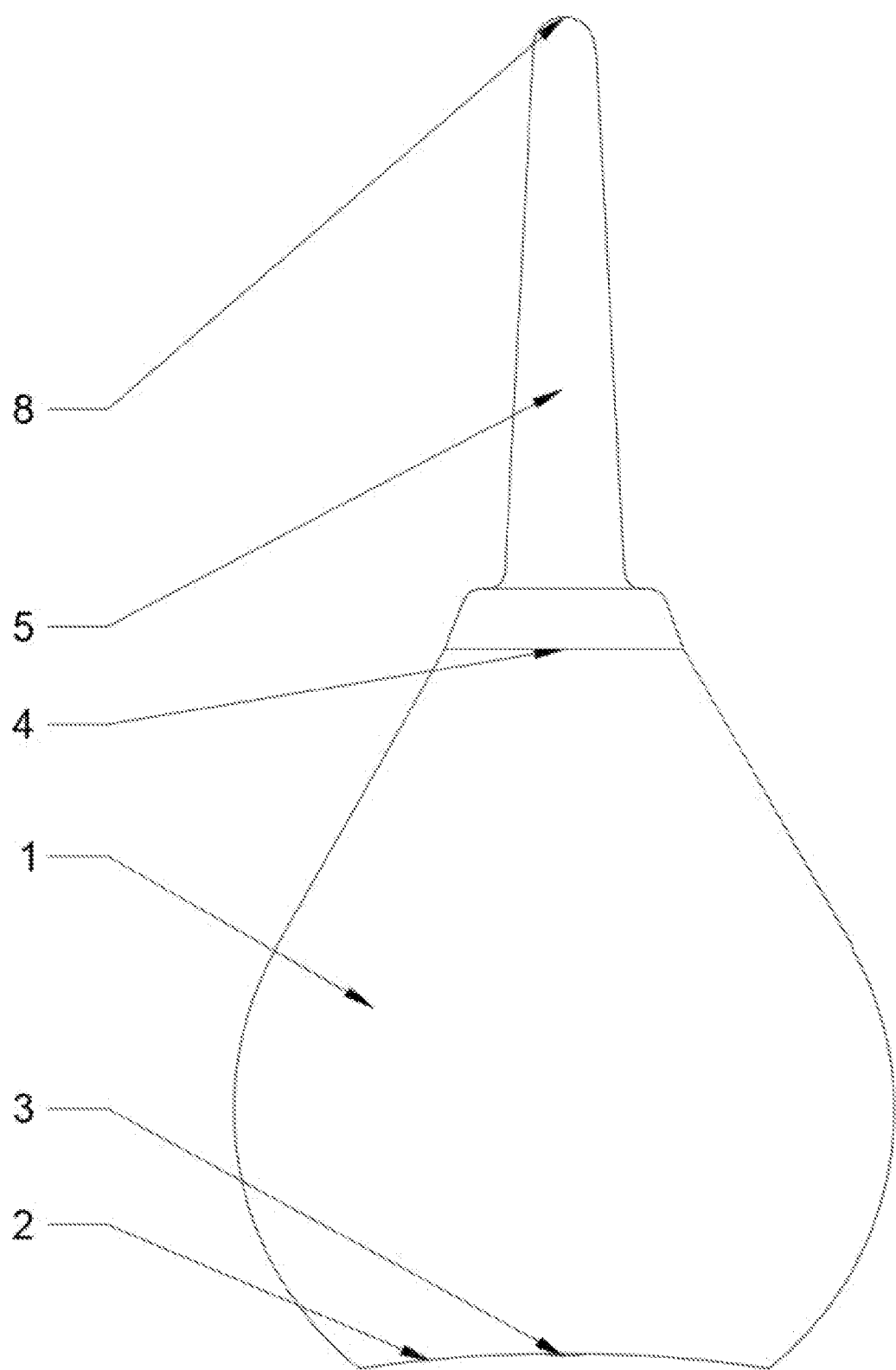
FIG. 1 is a schematic diagram of the structure of the anus cleaner of the invention.
Figure 2:
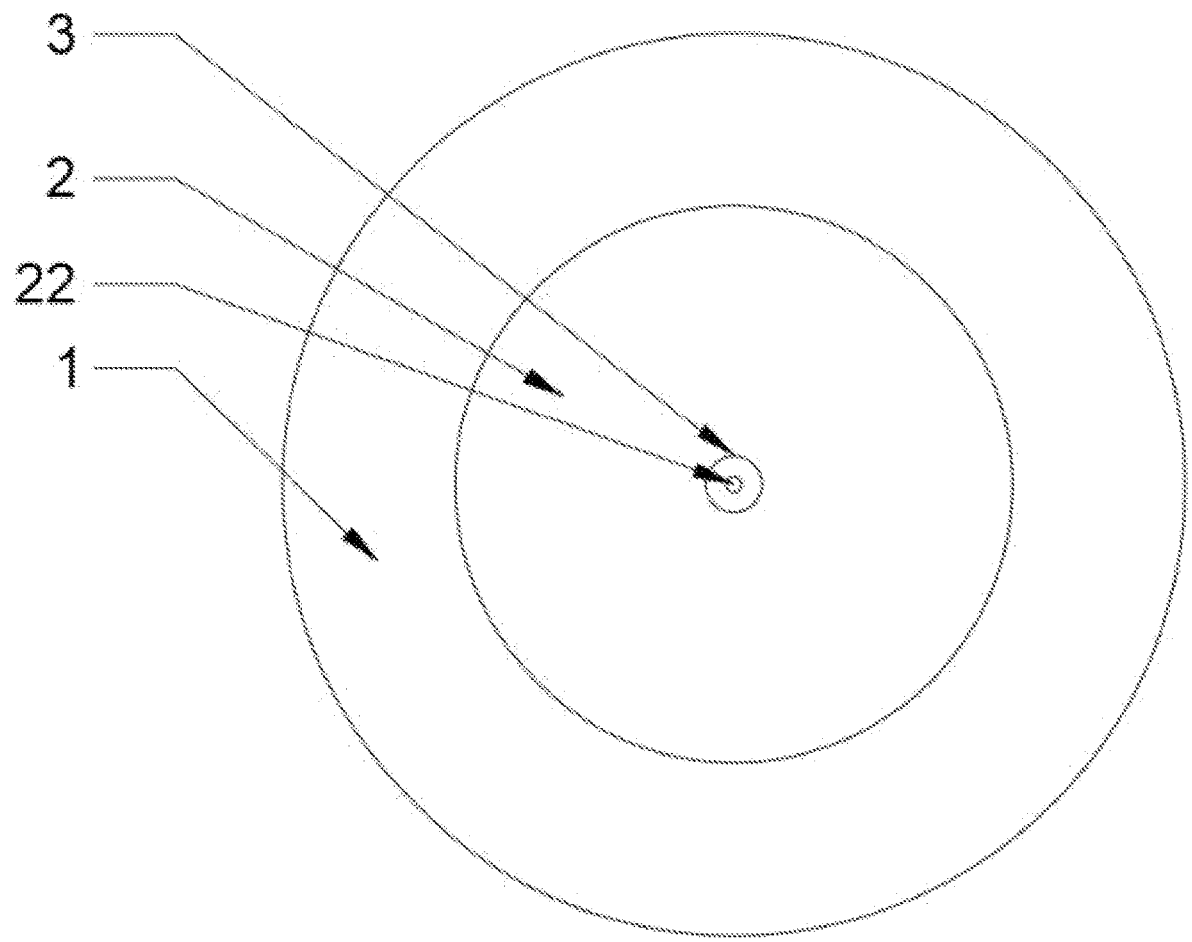
FIG. 2 is a bottom view of the anus cleaner of the invention.
Figure 3:
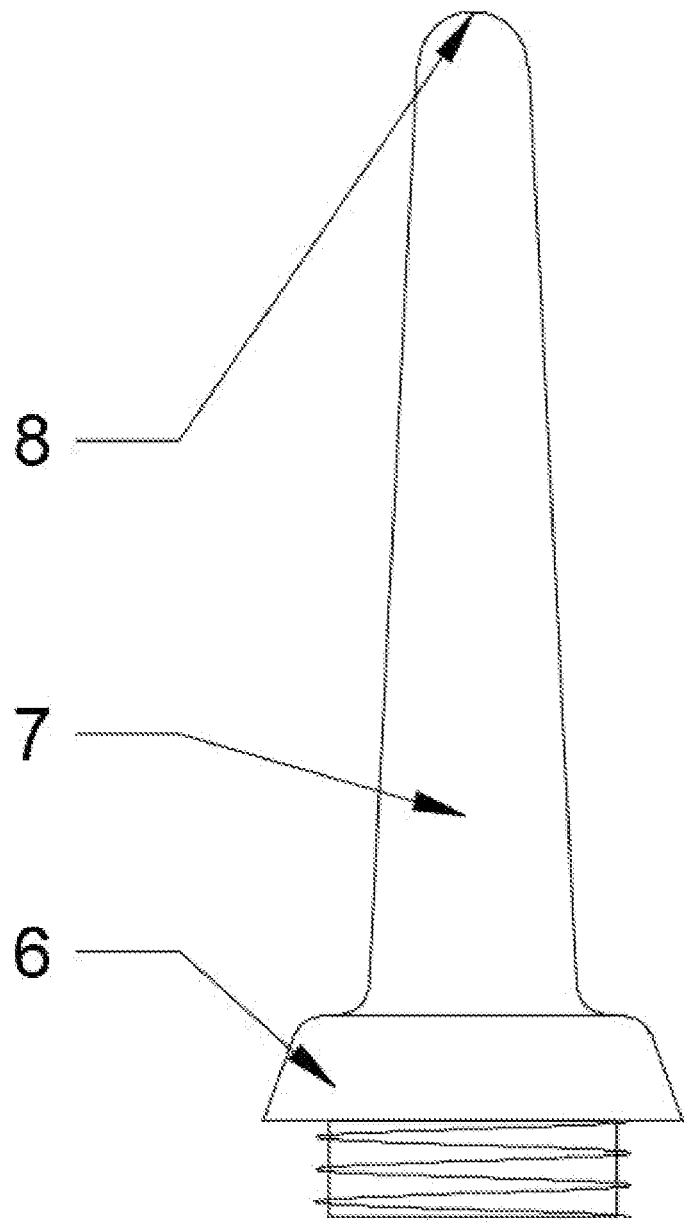
FIG. 3 is a schematic diagram of the structure of the cleaning head in the anus cleaner of the invention.
Figure 4:
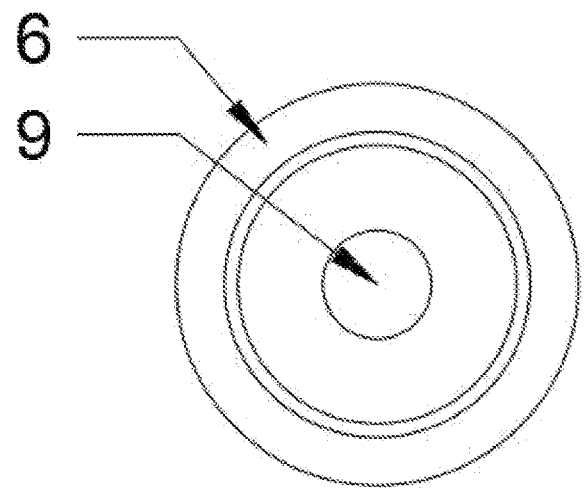
FIG. 4 is a bottom view of the cleaning head in the anus cleaner of the invention.
Figure 5:
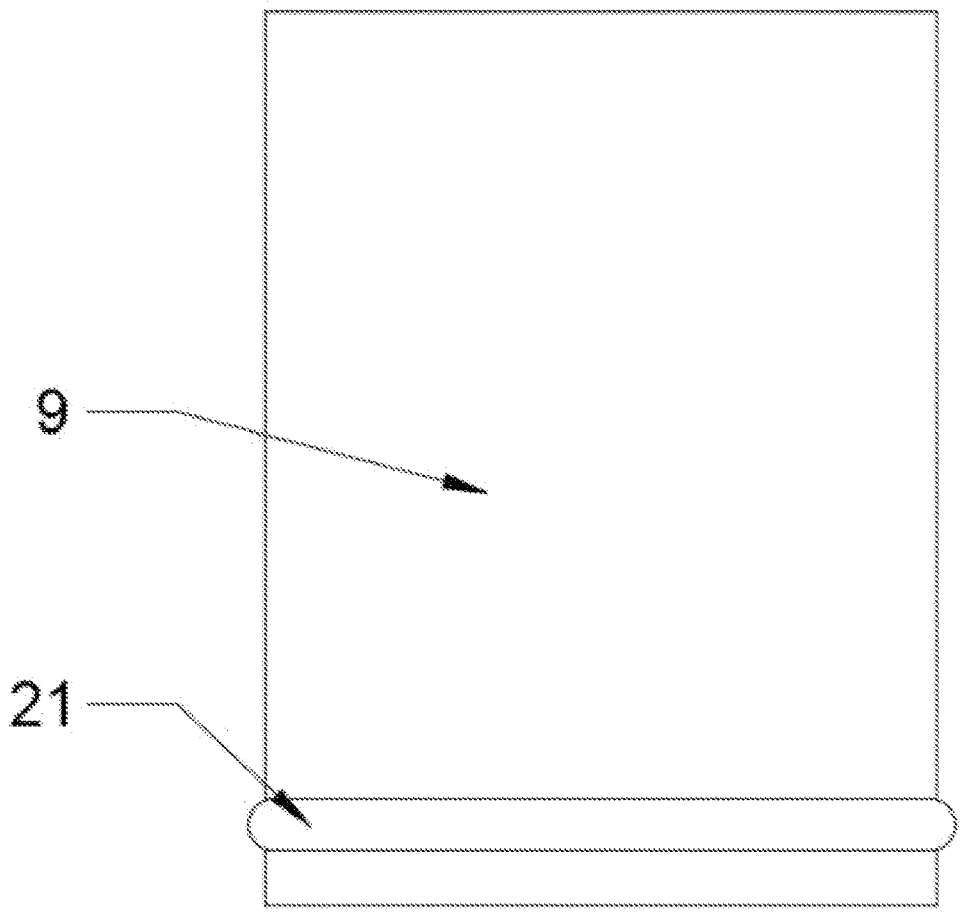
FIG. 5 is a schematic diagram of the structure of the spring check valve in the anus cleaner of the invention.
Figure 6:
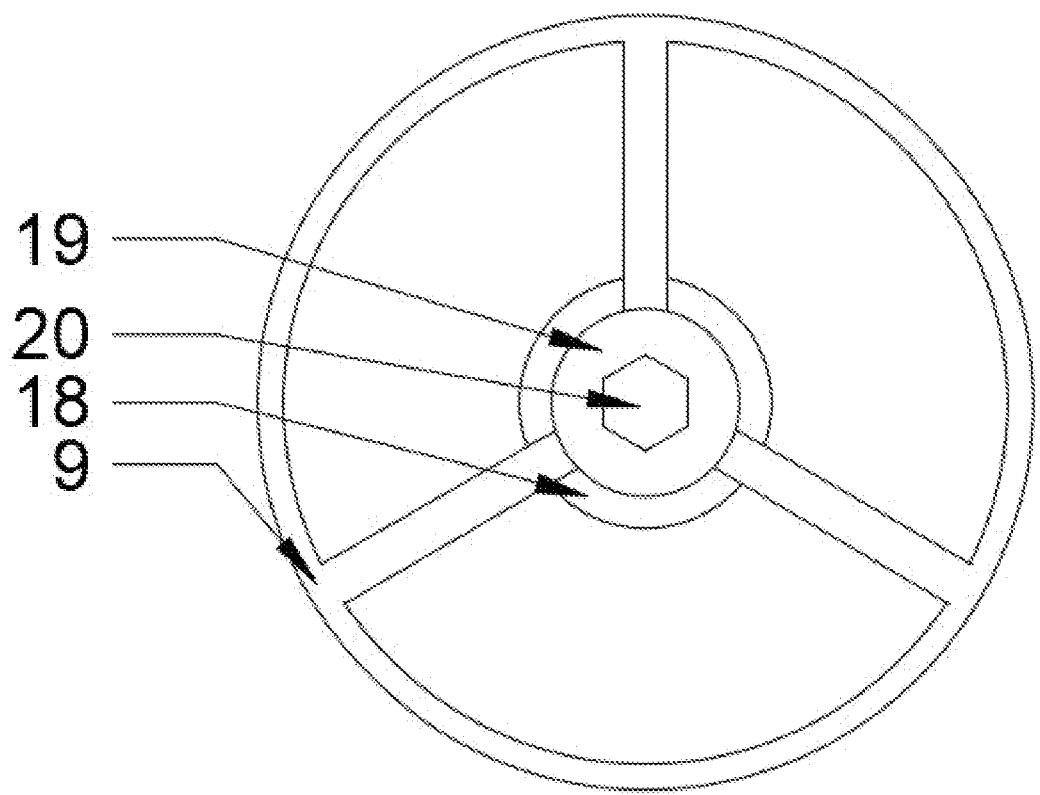
FIG. 6 is a top view of the spring check valve in the anus cleaner of the invention.
Figure 7:
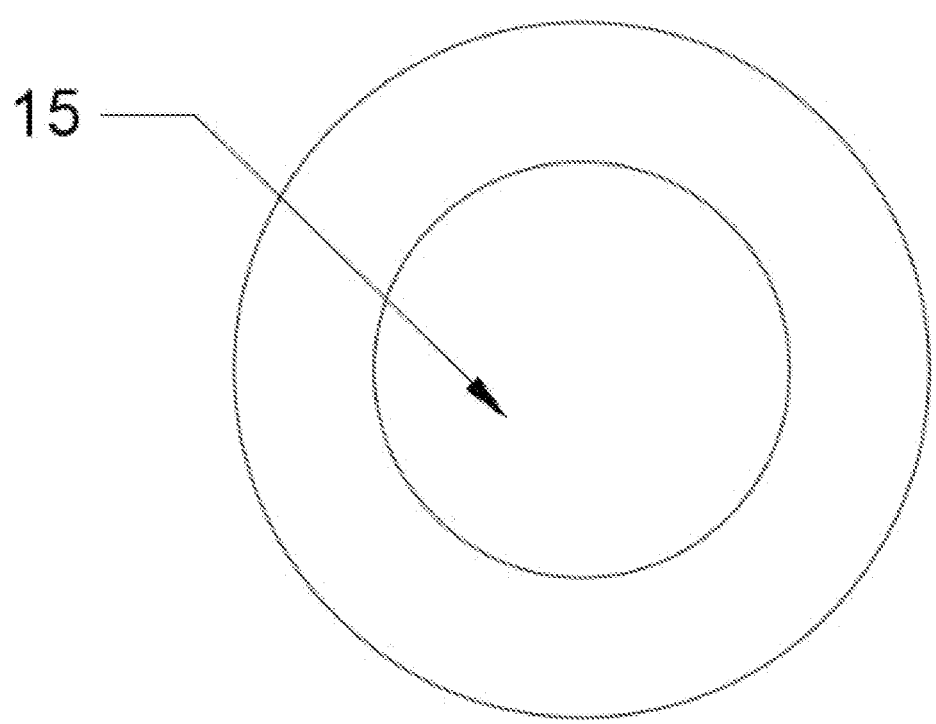
FIG. 7 is a bottom view of the spring check valve in the anus cleaner of the invention.
Figure 8:
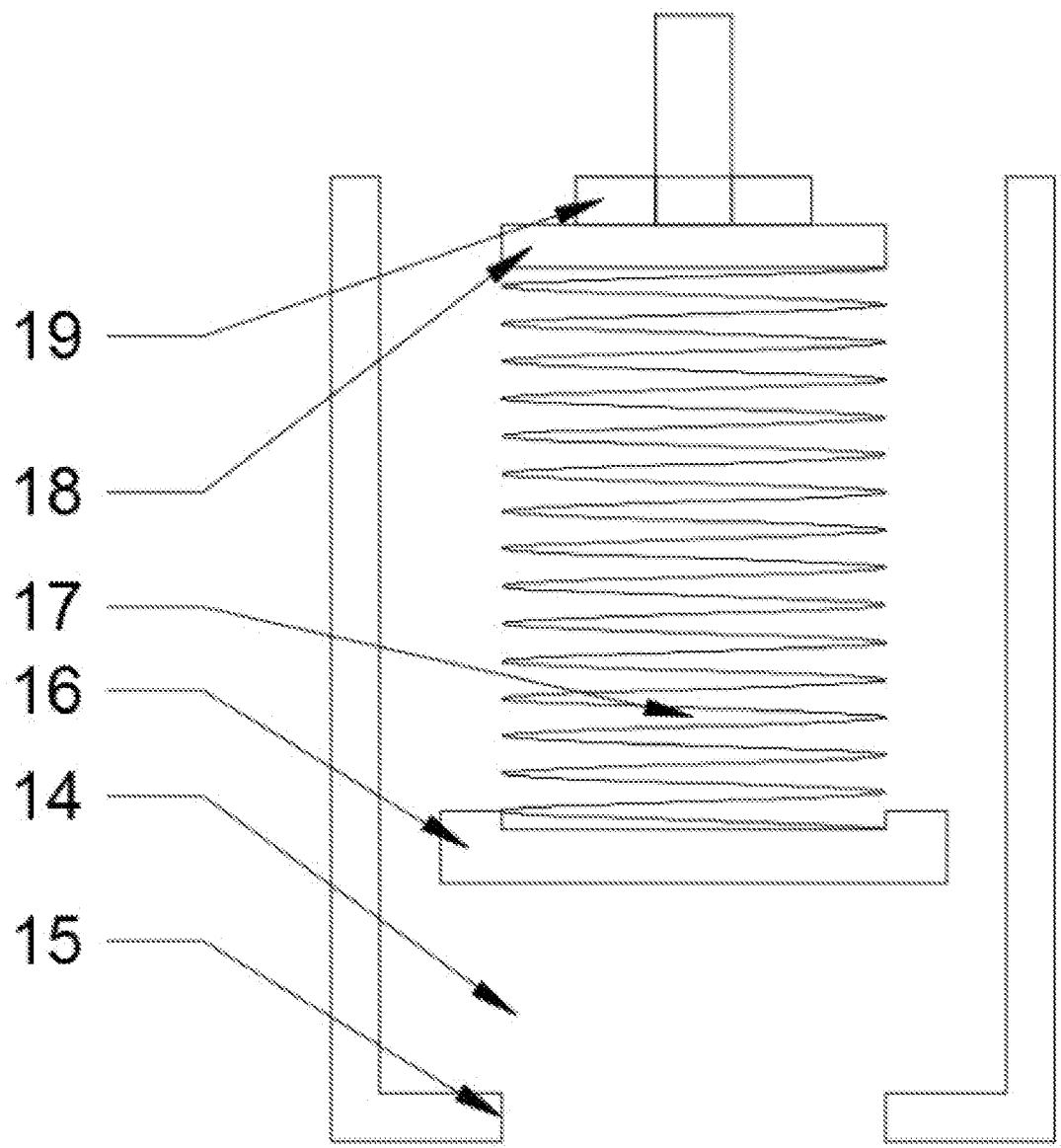
FIG. 8 is a cross-sectional view of the spring check valve in the anus cleaner of the invention.
Figure 9:
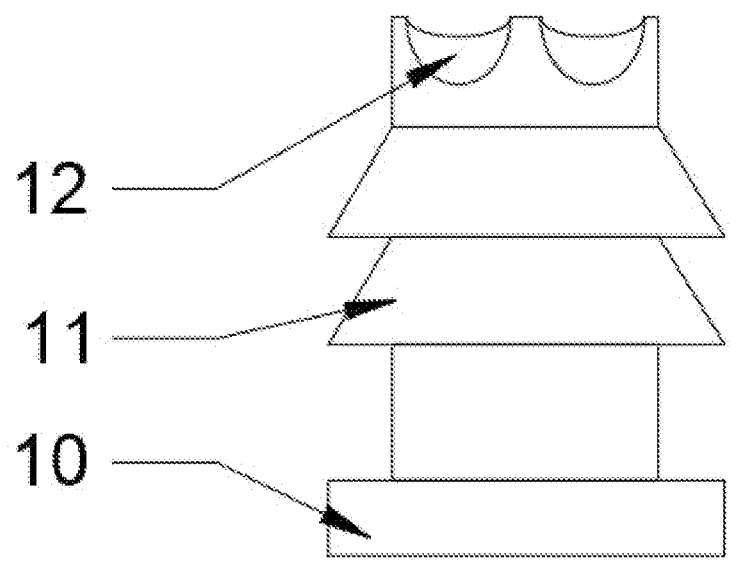
FIG. 9 is a schematic diagram of the structure of the steel ball check valve in the anus cleaner of the invention.
Figure 10:
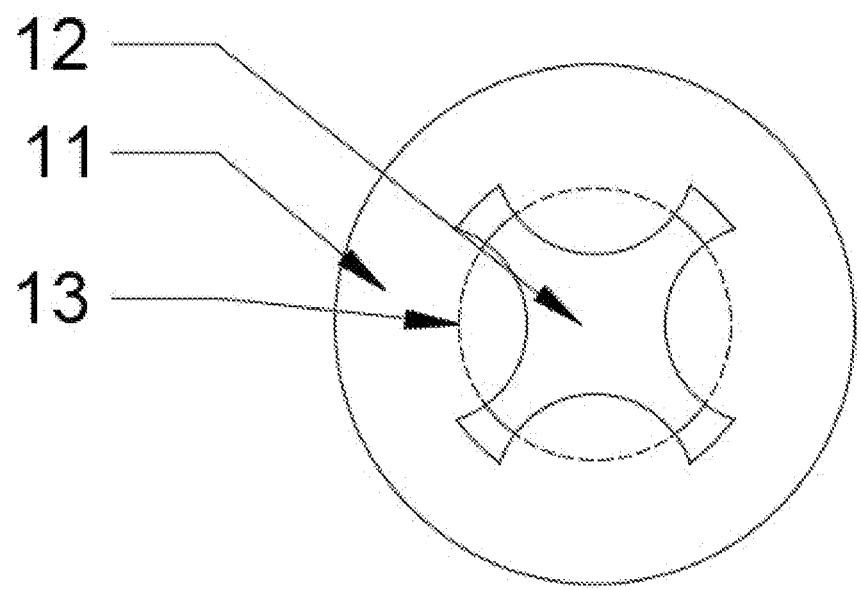
FIG. 10 is a top view of the steel ball check valve in the anus cleaner of the invention.
Figure 11:
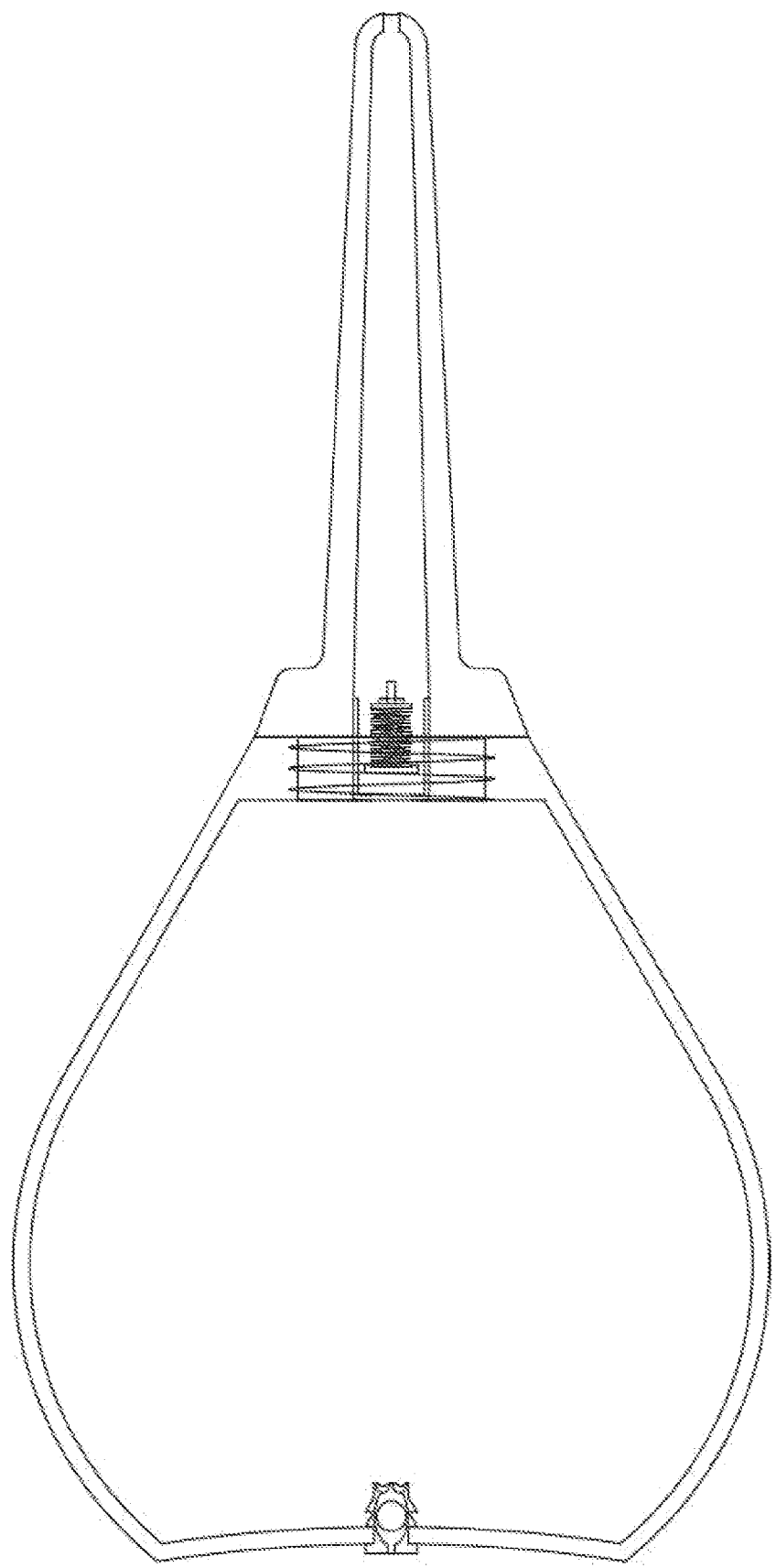
FIG. 11 is a cross-sectional view of the overall structure of the anus cleaner of the invention.
Figure 12:
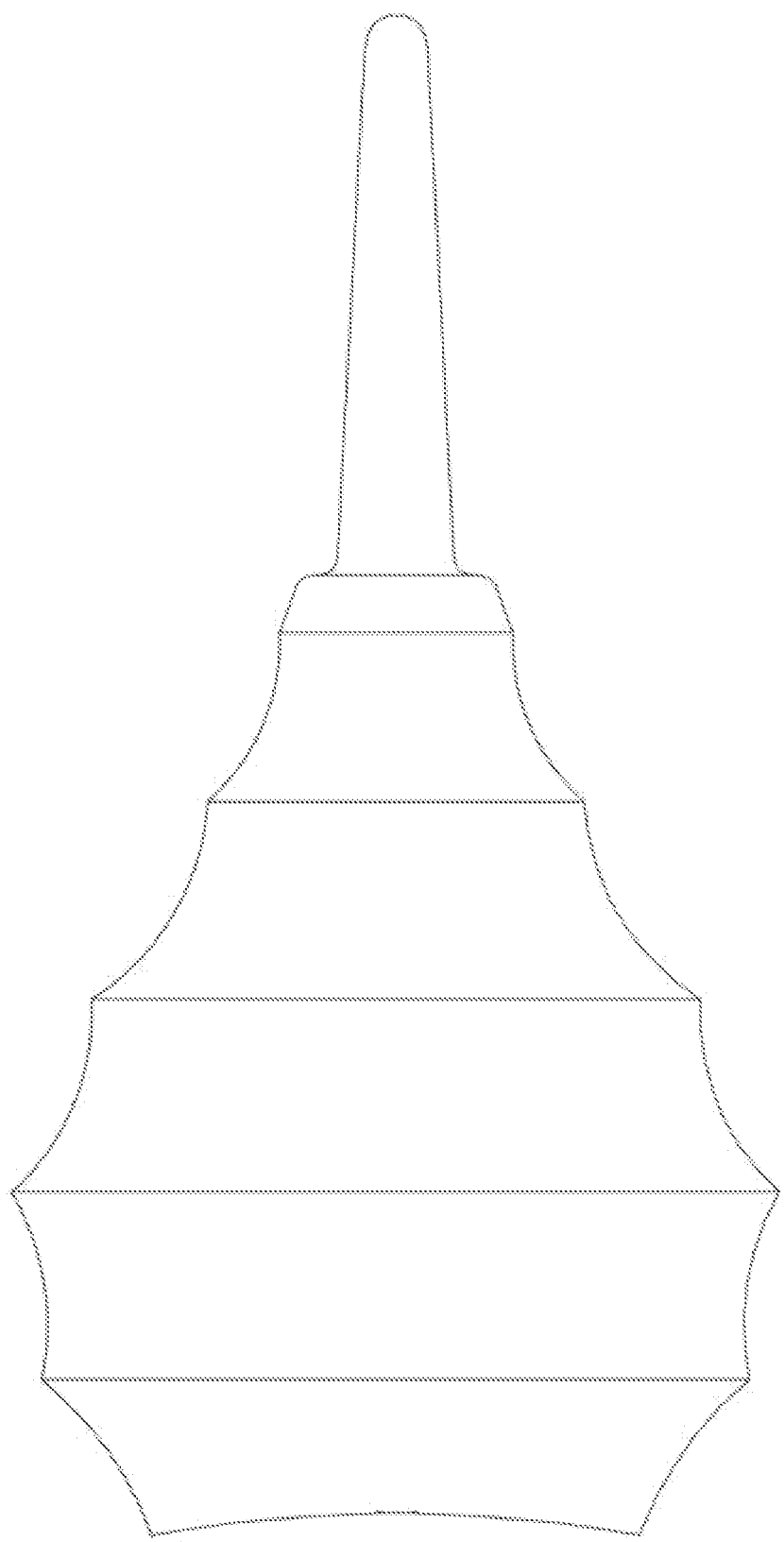
FIG. 12 is a schematic structural diagram of an embodiment of the anus cleaner of the invention.

As shown in the figures,
1 refers to the bottle body;
2 refers to the bottle bottom;
3 refers to the steel ball check valve;
4 refers to the bottleneck;
5 refers to the cleaning head;
6 refers to the mounting table;
7 refers to the cleaning neck;
8 refers to the liquid outlet;
9 refers to the spring check valve;
10 refers to the limiting seat;
11 refers to the limiting round table;
12 refers to the ball locking notch;
13 refers to the plugging steel ball;
14 refers to the movable cavity;
15 refers to the limiting port;
16 refers to the spring base;
17 refers to the spring;
18 refers to the plugger;
19 refers to the limiting ring;

20 refers to the limiting hole;
21 refers to the sealing ring;
22 refers to the inlet.

DETAILED DESCRIPTION OF THE PREFERRED EMBODIMENTS

The invention will be further described in detail hereinafter with reference to the drawings.

When the invention is in specific implementation, an anus cleaner, comprising a bottle body 1, wherein the inside of the bottle body 1 is a hollow structure; the bottom of the bottle body 1 is provided with a bottle bottom 2, and the bottle bottom 2 is curved; the center of the bottle bottom 2 is provided with a through hole, and a steel ball check valve 3 is installed in the through hole; the end of the bottle body 1 away from the bottle bottom 2 is provided with a bottleneck 4, and the bottleneck 4 is provided with threads; the bottleneck 4 is equipped with a cleaning head 5; the bottom of the cleaning head 5 is provided with threads, and the threads are provided on a mounting table 6; the mounting table 6 and the bottleneck 4 are matched and connected with the same size; the top of the mounting table 6 is provided with a cleaning neck 7; the inside of the cleaning head 5 is provided with a flow channel; the end of the cleaning neck 7 is provided with a liquid outlet 8; the center of the bottom of the mounting table 6 is provided with a spring check valve 9, and the spring check valve 9 communicates with the flow channel.

As an improvement, the bottom of the steel ball check valve 3 is provided with a limiting seat 10; and the center of the bottom of the limiting seat 10 is provided with an inlet 22; the inside of the steel ball check valve 3 is provided with a cavity; the top of the limiting seat 10 is fixed with limiting round tables 11, and the number of the limiting round table 11 is two; the top of the limiting round table 11 is fixed with a ball locking notch 12; the cavity inside the steel ball check valve 3 is placed with a plugging steel ball 13; cavity is oval shaped, and both ends thereof can be matched with the plugging steel ball 13.

As an improvement, the bottom of the spring check valve 9 is provided with a movable cavity 14, and the bottom of the movable cavity 14 is provided with a limiting port 15; a spring base 16 is installed inside the movable cavity 14 on the limiting port 15, and a spring 17 is installed on the spring base 16; the top of the spring 17 is installed with a plugger 18; the top of the spring check valve 9 is provided with a limiting ring 19, and the center of the limiting ring 19 is provide with a limiting hole 20; the limiting hole 20 is matched with the plugger 18; the bottom of the spring check valve 9 is installed with a sealing ring 21.

As an improvement, the outside of the bottle body 1 is a frosted surface, which is non-slip and easy to hold; the outside of the cleaning head 5 has a smooth surface for easy access.

As an improvement, the cleaning neck 7 is a tapered structure, and the diameter of the end thereof close to the liquid outlet 8 is smaller than the end close to the mounting table 6, which is used to reduce discomfort.

The working principle of the invention: the user needs to squeeze the bottle body when inhaling the liquid medicine. The bottle body is made of rubber material. After squeezing, negative pressure is formed in the bottle. Since the bottleneck faces the liquid medicine, the steel ball at the bottom falls due to gravity, and then presses firmly on the ball locking notch to form a seal under atmospheric pressure. In the process of drug delivery, the spring limiting piece is contracted due to the liquid pressure inside the bottle, and the liquid flows into the anus through the check valve. Since the bottle body is upside down, the steel ball falls, but the internal pressure of the bottle body is stronger than atmospheric pressure, so the steel ball is pushed to block the inlet, providing sufficient pressure inside the bottle body. After the liquid medicine is squeezed out, the steel ball falls and the bottle body starts to inhale; at this time, under the action of the spring, the spring base presses against the limiting port to form a hermetic seal to prevent backflow.

EMBODIMENT

The bottle body is made transparent with edges and corners as a scale, which is not only practical, but also beautiful, avoiding the straight cylindrical shape of the traditional bottle body.

In addition, the terms "first" and "second" are only used for descriptive purposes, and cannot be understood as indicating or implying relative importance or implicitly indicating the number of indicated technical features. Thus, the features defined with "first" and "second" may explicitly or implicitly include one or more of these features. In the description of the invention, unless otherwise clearly defined, "plurality" means two or more.

In the invention, unless otherwise clearly defined and limited, the terms "installed", "communicated", "connected", "fixed" and other terms should be interpreted broadly; for example, it can be a fixed connection, it can be a detachable connection, or integrated; it can be a mechanical connection or an electrical connection; it can be a direct connection, or an indirectly connection through an intermediate medium, and it can be an internal communication between two elements or the interaction relationship between two elements, unless specifically defined otherwise. For those of ordinary skill in the art, the specific meaning of the above terms in the invention can be understood according to specific circumstances.

In the invention, unless otherwise clearly defined and limited, the first feature is "above" or "below" the second feature can be that the first feature and the second feature are in direct contact, or the first feature and the second feature are not in direct contact but in contact with another feature between them. Moreover, the first feature is "above", "over", and "in the upper of" the second feature can be that the first feature is directly above and obliquely above the second feature, or only that the level of the first feature is higher than that of the second feature. The first feature is "below", "under", and "in the lower of" the second feature can be that the first feature is directly below and obliquely below the second feature, or only that the level of the first feature is lower than that of the second feature.

In the description of the specification, description with reference to the terms "one embodiment", "some embodiments", "examples", "specific examples", or "some examples" etc. means that the specific features, structures, materials, or characteristics described in conjunction with the embodiments or examples are included in at least one embodiment or example of the invention. In the specification, the schematic representation of the above terms does not necessarily refer to the same embodiment or example. Moreover, the described specific features, structures, materials or characteristics may be combined in any one or more embodiments or examples in a suitable manner.

Although the embodiments of the invention have been shown and described hereinabove, it can be understood that the above embodiments are exemplary and should not be understood as limiting the invention. Those of ordinary skill in the art can make changes, modifications, substitutions and variations to the above embodiments within the scope of the invention without departing from the principle and purpose of the invention.

The invention claimed is:

1. An anus cleaner, comprising: a bottle body (1), wherein an inside of the bottle body (1) is a hollow structure; a bottom of the bottle body (1) is provided with a bottle bottom (2), and the bottle bottom (2) is curved; a center of the bottle bottom (2) is provided with a through hole, and a steel ball check valve (3) is installed in the through hole; an end of the bottle body (1) away from the bottle bottom (2) is provided with a bottleneck (4), and the bottleneck (4) is provided with threads; the bottleneck (4) is equipped with a cleaning head (5); a bottom of the cleaning head (5) is provided with threads, and the threads are provided on a mounting table (6); the mounting table (6) and the bottleneck (4) are connected; a top of the mounting table (6) is provided with a cleaning neck (7); an inside of the cleaning head (5) is provided with a flow channel; an end of the cleaning neck (7) is provided with a liquid outlet (8); a center of a bottom of the mounting table (6) is provided with a spring check valve (9), and the spring check valve (9) communicates with the flow channel;

a bottom of the steel ball check valve (3) is provided with a limiting seat (10); and a center of the bottom of the limiting seat (10) is provided with an inlet (22); an inside of the steel ball check valve (3) is provided with a cavity; a top of the limiting seat (10) is fixed with limiting round tables (11), and the number of the limiting round tables (11) is two; a top of the limiting seat (10) is fixed with two limiting round tables (11); a top of each limiting round table (11) is fixed with a ball locking notch (12); the cavity inside the steel ball check valve (3) is placed with a plugging steel ball (13); the cavity is oval shaped, and both ends thereof can be matched with the plugging steel ball (13).

2. The anus cleaner according to claim 1, wherein a bottom of the spring check valve (9) is provided with a movable cavity (14), and a bottom of the movable cavity (14) is provided with a limiting port (15); a spring base (16) is installed inside the movable cavity (14) on the limiting port (15), and a spring (17) is installed on the spring base (16); a top of the spring (17) is installed with a plugger (18); a top of the spring check valve (9) is provided with a limiting ring (19), and a center of the limiting ring (19) is provided with a limiting hole (20); the limiting hole (20) is matched with the plugger (18); the bottom of the spring check valve (9) is installed with a sealing ring (21).

3. The anus cleaner according to claim 1, wherein an outside of the bottle body (1) is a frosted surface, which is non-slip; an outside of the cleaning head (5) has a smooth surface for easy access.

4. The anus cleaner according to claim 1, wherein the cleaning neck (7) is a tapered structure, and a diameter of an end thereof close to the liquid outlet (8) is smaller than the end close to the mounting table (6), which is used to reduce discomfort.

* * * * *